United States Patent [19]

Toyoshima et al.

[11] 4,287,185

[45] Sep. 1, 1981

[54] METHOD FOR THE DETECTION OF VIRUSES

[75] Inventors: Kumao Toyoshima, Suita; Akira Hakura, Toyonaka; Toshihiro Nakanishi, Ibaraki; Hajime Yoshizumi, Takatsuki, all of Japan

[73] Assignee: Suntory Ltd., Osaka, Japan

[21] Appl. No.: 82,657

[22] Filed: Oct. 9, 1979

[30] Foreign Application Priority Data

Oct. 9, 1978 [JP] Japan ............................. 53-124412

[51] Int. Cl.³ ................... A61K 37/00; C07C 103/52
[52] U.S. Cl. .............................. 424/177; 260/112.5 R
[58] Field of Search ................. 424/177; 260/112.5 R

[56] References Cited

PUBLICATIONS

Mak et al., Canadian Journal of Biochemistry 22, No. 10, (1976), 836–842.
Ohtani et al., Agr. Biol. Chem. 39, (11), 2269–2270, (1975).
Jones et al., Cereal Chem. 54, (3), 511–523, (1976).

*Primary Examiner*—Delbert R. Phillips
*Attorney, Agent, or Firm*—Birch, Stewart, Kolasch & Birch

[57] ABSTRACT

Certain novel polypeptides and their use as carcinostatic agents and as agents for the detection and determination of viruses. The polypeptides contain forty-five amino acid residues and have a peculiar tetracyclic structure in that they are bridged with four disulfide bonds between each cysteine molecular pair, said pairs being present between the 3rd and the 39th, 4th and 31st, 12th and 29th and 16th and 25th positions, respectively.

9 Claims, 4 Drawing Figures

METHOD FOR THE DETECTION OF VIRUSES

The present invention relates to certain novel polypeptides. The invention is also directed to carcinostatic agents and agents for the detection and determination of viruses containing the novel polypeptides as an effective component thereof.

More particularly, this invention relates to carcinostatic agents as well as detection and/or determinative agents for viruses which contain the following two kinds of novel polypeptides having the following generic formula (primary structural formula):

wherein the symbols "Ala", "Arg", "Asn", "Cys", "Gln", "Gly", "Leu", "Lys", "Phe", "Pro", "Ser", "Thr", "Tyr" and "Val" indicate, respectively, the residues of the levo rotatory forms of alanine, arginine, asparagine, ½ cystine, glutamine, glycine, leucine, lysine, phenylalanine, proline, serine, threonine, tyrosine and valine, and wherein $R_1$-$R_5$ mean (1) the residues of the following L-amino acids, respectively:

$R_1$: lysine
$R_2$: asparagine
$R_3$: leucine
$R_4$: threonine
$R_5$: aspartic acid or (2) where $R_1$ is arginine, $R_2$ and $R_5$ are glycine, $R_3$ is isoleucine and $R_4$ is serine, respectively. The symbols "=" represent —S—S— bonds and, further, the arabic numerals included in the structural formula near certain amino acid residues constitute the sequence number of said amino acids in turn from the N-terminal.

The first analog of the novel polypeptides of the invention (hereinafter referred to as "SP₁") consists of forty-five amino acid residues and has the following primary structural formula:

wherein all of the symbols for the respective amino acid residues are the same as described hereinabove. This analog has a peculiar tetracyclic structure in that it is bridged with four disulfide bonds between each cysteine molecular pair, said pairs being present between the 3rd and 39th, the 4th and 31st, the 12th and 29th and the 16th and 25th positions, respectively.

The second analog of the novel polypeptides of the invention (hereinafter referred to as "SP₂") also consists of 45 amino acid moieties and has the following primary structural formula:

wherein all of the symbols for the respective amino acid residues are the same as described above. This analog also has a peculiar tetracyclic structure in that it is bridged with disulfide bonds in the same manner as the analog SP₁.

These two analogs can be characterized by the following physical and chemical parameters:

(SP₁):

Appearance: colorless, needle-like crystals
Isoelectric point: ca. pH 10
Molecular weight (MW): 4913 calculated from amino acid sequencing, but the MW is further estimated to be ca. 5500 according to a sedimentation equilibrium method. The latter determination was obtained by dissolving the sample in 0.05M tris-HCl buffer containing 6M guanidine. HCl in the concentration of 1 to 5 mg/ml and measuring at 17,600 rpm by a Spinco Model E ultracentrifuge (Beckman Co.).

Number of amino acid moieties: 45
Amino acid sequence:

The abbreviations and numerals have the same meaning as set forth above.

| Elemental analysis: | | | | |
|---|---|---|---|---|
| | C | H | N | S |
| calculated | 49.56 | 6.84 | 19.07 | 5.21 |
| found | 49.32 | 6.94 | 18.92 | 5.34 |

Ultraviolet absorption spectrum (FIG. 3): A characteristic absorption due to peptides was observed in the vicinity of 278 nm. Samples of 2 mg/ml were measured by the Hitachi Two Wave Double-Beam Spectrophotometer (Type 356).

Infrared absorption spectrum (FIG. 4): A characteristic absorption due to peptides was observed in the vicinity of 1600 cm$^{-1}$ (measured by a Hitachi Lattice Infrared Spectrophotometer).

Amino Acid Composition: These results are shown in Table 1. The samples were hydrolyzed with 6N HCl at 110° C. in an evacuated sealed tube and measured by an amino acid analyzer (Type JLC 5 AH of Nippon Denshi Co., Ltd.).

TABLE 1

| Amino acids | Molar amount (found) | Nearest Integers (the number of assumed amino acid moieties) |
|---|---|---|
| AsN(ASP + Asn) | 4.02 | 4 |
| Thr | 1.94 | 2 |
| Ser | 4.00 | 4 |
| GlX(Glu + Gln) | 1.01 | 1 |
| Pro | 2.11 | 2 |
| Gly | 3.11 | 3 |
| Ala | 3.12 | 3 |
| ½ Cys | — | 8* |
| Val | 0.88 | 1 |
| Met | 0.00 | 0 |
| Ile | 0.00 | 0 |
| Leu | 4.76 | 5 |
| Tyr | — | 1* |
| Phe | 1.01 | 1 |
| Lys | 6.08 | 6 |
| His | 0.00 | 0 |
| Arg | 4.11 | 4 |
| Trp** | 0.00 | 0 |

*From amino acid sequencing.
**Measured by spectrophotometry.

Gel electrophoresis: A single band was observed as the result of polyacrylamide disc electrophoresis. This measurement was carried out in 7.5% polyacrylamide gel at pH 9.4 and 4.0. The upper electrode was connected to the anode, and electrophoresis was carried out at 25 mA/cm² for 50 minutes at room temperature. The gel was stained with 0.02% Coomassie Brilliant Blue R and then destained with 10% trichloroacetic acid.

(SP$_2$):

Molecular weight: 4812 (from the result of amino acid sequencing). However, the MW was estimated to be ca. 5500 according to a sedimentation equilibrium method with an ultracentrifuge as described in connection with SP$_1$.

Number of amino acid moieties: 45

Amino acid sequence:

Lys—Ser—Cys—Cys—Arg—Ser—Thr—Leu—Gly—Arg—
Asn—Cys—Tyr—Asn—Leu—Cys—Arg—Ala—Arg—Gly—
Ala—Gln—Lys—Leu—Cys—Ala—Gly—Val—Cys—Arg—
Cys—Lys—Ile—Ser—Ser—Gly—Leu—Ser—Cys—Pro—
Lys—Gly—Phe—Pro—Lys

The abbreviations and numerals have the same meaning as set forth above.

| Elemental analysis: | | | | |
|---|---|---|---|---|
| | C | H | N | S |
| calculated | 49.34 | 6.94 | 19.77 | 5.32 |
| found | 49.21 | 6.52 | 19.92 | 4.92 |

Ultraviolet absorption spectrum (FIG. 3): A characteristic absorption due to peptides was observed in the vicinity of 278 nm.

Infrared absorption (FIG. 4): A characteristic absorption due to peptides was observed in the vicinity of 1600 cm$^{-1}$.

Amino Acid Composition: The results are shown in Table 2. Analysis was conducted in the same manner as described in connection with Table 1 above.

TABLE 2

| Amino acids | Molar amount (found) | Nearest Integers (the number of assumed remaining radicals) |
|---|---|---|
| AsN(Asp + Asn) | 2.16 | 2 |
| Thr | 1.10 | 1 |
| Ser | 4.92 | 5 |
| GlX(Glu + Gln) | 1.04 | 1 |
| Pro | 2.13 | 2 |
| Gly | 4.88 | 5 |
| Ala | 3.05 | 5 |
| ½ Cys | — | 8* |
| Val | 0.84 | 1 |
| Met | 0.00 | 0 |
| Ile | 0.95 | 1 |
| Leu | 3.89 | 4 |
| Tyr | — | 1* |
| Phe | 1.00 | 1 |
| Lys | 4.81 | 5 |
| His | 0.00 | 0 |
| Arg | 4.95 | 5 |
| Trp** | 0.00 | 0 |

*From amino acid sequencing.
**Measured by spectrophotometry.

Gel electrophoresis: A single band was observed as the result of polyacrylamide disc electrophoresis.

As is clear from the above results, SP$_1$ and SP$_2$ are mutually quite alike physically and chemically and, hence, separation of each other from a mixture is difficult without chromatography with a cation-exchangeable absorbent such as carboxymethyl (CM) cellulose.

SP$_1$ and SP$_2$ and analogs thereof are widely distributed in barley and wheat.

An exemplary procedure for obtaining SP is illustrated in the following.

4 Kg of wheat flour was suspended in 20 liters of 0.05 N H$_2$SO$_4$ and kept at 30° C. for 3 hours. After removal of precipitate by centrifugation (3000 rpm, 10 minutes, room temperature), the supernatant was neutralized with 10 N NaOH and left to stand for 12 hours at 50° C. The resulting precipitate was removed by centrifugation, and the supernatant was chromatographed on a CM cellulose column (2.5×80 cm) equilibrated with 0.05 M phosphate buffer, pH 7.2 and eluted with a linear gradient of 0.1 to 0.8 M NaCl in the same buffer (700 ml in each reservoir) at room temperature. The flow rate was monitored by the absorption at 280 rm. The eluate was chromatographed again by a similar column (1.5×75 cm), if desired, and then lyophilized. Yield: 120 mg.

120 Mg of the above dried matter was loaded on a CM cellulose column (3.1×33 cm) buffered with 0.2 M ammonium bicarbonate solution and then eluted with a gradient of 0.2 to 0.8 M ammonium bicarbonate solution at a velocity of 66 ml/hr. The eluate was then fractionated into 13 ml each being monitored by the absorption at 280 rm. Thus, two kinds of absorptive fractions, fraction Nos. 63 to 75 and 80 to 89 were collected, respectively.

The present invention is further illustrated by reference to the specific examples in the following specification and the accompanying drawings wherein.

One of the primary objectives of the present invention is to use the above-described novel polypeptides as a carcinostatic agent and as an agent for detecting and determining viruses.

It has previously been reported that certain acidic peptides for some microorganisms show some antitumor properties. For example, Beerman et al (1977) have recently reported that neocarzinostatin of which the amino acid sequence was determined by Meinhofer et al (1972) will act as an inhibitor against cell division by connecting to the DNA double-chains of the cells and then cutting said chain.

On the other hand, it has been observed that tumor cells are different in some characteristics from normal cells. As the most characteristic of tumor cells, there can be pointed out the decrease in contact inhibition ability and the variation in the cell membranes together with other symptoms. For example, the difference between tumor cells and normal cells is visualized by an in vitro cultivation. In the latter, the growth of the cells will stop when they have grown and become arranged monolamellarly on the inner bottom surface of the dish; on the contrary, in the former, the growth of the cells does not stop and continues without limit over the monolamellar stage without such stagnation. Namely, one of the characteristic features of tumor cells is the limitless growth thereof. Thus, it can be presumed that in tumor cells, there will be seen a repeated cycle of cell growth different from normal cells and, therefore, in the course of the tumor cell growth, the following cycle occurs:

G$_1$: preparatory phase for DNA synthesis (phase for pre-DNA synthesis)
S: DNS synthesis phase
G$_2$: preparatory term for segmentation (phase for post-DNA synthesis)
M: segmentation phase
G$_0$: stagnant phase of segmentation This cycle certainly passes through the phase for DNA synthesis.

Then, as shown by Ben-Or et al (Nature, 188, 1200 (1961) and other investigators, in the surface of a cell membrane (superficial layer), the surface changes in charge density and becomes strongly negative-charged as the liver cell grows up. Contrary to this, the cause of the increase in the charge density on the surface of tumor cells may be assumed to be an acceleration of the multiplying function (especially of the DNA synthesis function).

The transformation of normal cells to tumor cells may be caused by a virus, rather than by physico-chemical factors such as chemical substances, ultraviolet rays, radiation, etc. Also, in the cells which have been turned into tumor cells by infection of a tumor virus, it can generally be seen that its surface charge condition becomes more negative and that its superficial structure changes to a condition in which the cells are vigorously multiplied, in other words, a condition alike to that of the S-phase in the cell cycle. Indeed, some carcinostatic substances which appear to be based on such features of the tumor cells have been reported. As the typical substance among them, poly-DL-lysine (average polymerization degree of 240) has a recognized carcinostatic action.

As the result of the investigations of the present inventors directed to the physiological action of the novel polypeptides, SP$_1$ and SP$_2$ (generally called "SP" herein), as aforementioned, said compounds being isolated from wheat grain and the chemical structure thereof determined as described above, it has been found that this SP will peculiarly and selectively act with respect to animal cells at the S-phase (DNA synthetic phase) and will kill said cells, while exhibiting a weak action against other cells at any stage other than the S-phase. In particular, said SP does not act against normal cells in the state of contact inhibition.

Many cells comprising animal tissue can generally be regarded as being in the $G_0$ phase. Thus, while SP of the present invention is fatal to cells in the segmentation phase (tumor cells) in living bodies, it is to be noted that this substance will not affect normal cells in the state of contact inhibition. Hence, a novel finding of the invention comprises such basic proteins that have the property of very selectively and peculiarly acting on cells which are in a special condition and killing them so as to stop or inhibit further tumor growth.

More specifically, SP shows its strong cell killing action only against cells in the multiplication phase. Generally, because it has been well known that there is a similarity between the multiplication of tumor cells and that of animal cells, the fact that SP is fatal to cells in the S-phase at first provides a perspective for utilizing this substance as an antitumor agent having a novel function and mechanism. As mentioned in the latter, this assessment was supported by in vivo tests with cancered animals. The second possibility based on the above is to use this substance as an agent for detecting and determining viruses.

At present, cultivation of viruses with animal and plant cells is used for many investigative and practical purposes such as the isolation of a virus, studies as to its properties, manufacture of vaccines, prevention and medical treatment of virus diseases, etc. However, in order to conduct such research and development, a premise to be preliminarily settled is that any virus can exactly and conveniently be detected and/or determined.

Means utilized for this purpose are as follows:

(1) Method in which visible cellular degeneration of virus-infected cells is measured as the parameter. (Cellular degeneration)

(2) Method by hemagglutination phenomenon caused by mixing erythrocytes with virus-infected cells. (Hemagglutination method)

(3) Method by interference phenomenon between a virus-infected cell and other viruses; the infections caused by the latter viruses will be inhibited. (Interference method)

(4) Method with a specific antiserum which is specifically reactive to a specific virus. (Antiserum method)

(5) Method by a metabolic change of cells caused by the virus infections. (Measurement of metabolic change)

(6) Method by microscopy directly or after staining. (Microscopic method)

Among these methods, method (1) is the most general, but there are many viruses not detectable by this method, such as, for example, murine leukemia virus (Mo-Mu LV). Moreover, even if some viruses are detectable in some manner according to the above methods (1) to (6), such methods are, from a practical point of view, hardly applicable as is, if either the judgement obtained is not clear and conclusive or the procedures therefor are too troublesome. Thus, many improvements have been previously proposed. For example, Rowe et al (Virology, 42, 1136-9 (1970)) cultured cells infected with the above Mo-LuLV with mouse embryo cells (ME), then stopped their growth by ultraviolet ray irradiation followed by cultivation with XC cells (rat tumor cells cancerized by plaque strains of Raus' sarcome virus), and then measured the number of the plaques thus formed after staining. This measurement is a utilization of the special property of the XC cell, said cell readily forming syncytium with the virus grown by virus infected cells, and therefore, it is, so to speak, an indirect detection and determination (assay) of the virus. Therefore, it is an inevitable fact that the object of this measurement is naturally limited to a special virus which forms syncytium as compared with a direct measurement such as the cellular degeneration method. Alternatively, an antiserum method is partly used for such measurement but the preparation of the antiserum is very troublesome and time-consuming. Moreover, such methods are only applicable to specific viruses. For these reasons, there has been an earnest need to develop a method for the detection and assay of viruses, which is more convenient, more exact and versatile, as a reliable guide for virus study.

However, this problem has been solved in accordance with the present invention by applying the above unique character of SP, being fatal to virus-infected cells, to this objective.

It is to be noted that the aforementioned mouse leukemia virus does not show a cysto-degeneration action to the host cells. Namely, this is an example in which the conventional direct detection or assay of viruses by the cysto-degeneration effect is not applicable, since nothing to be differentiated between the virus-infected cells and vice-versa according to microscopic observation, DNA synthesis, etc. can be seen. However, as the result of the experiments conducted by the present inventors, it has now been clear, when SP is applied to cells in the state of contact inhibition, for example, to $A_{31}$ cells (a clone derived from mouse BLAB/C), that only the virus-infected cells are killed but healthy (not infected) cells are not affected and that this selective fatal action is almost quantitative. This result is in accordance with that found by Rowe's XC cell measurement (XC plaque method). Besides, because the number of original viruses is calculated from the number of syncytium formed by scattering of the XC cells in this XC plaque method, it is naturally impossible to isolate virus-insensitive cells or non-infected cells as they are living cells (the original cells have become static due to ultraviolet ray irradiation and further the XC cells have been added into the culture.).

But, according to the present means in which SP is directly added into the culture, the procedure is far more simple at first, and further, it has a certain merit in that the surviving cells (survival due to deficiency in the amount of virus, mutation of said cells, etc.) can be used for numerous studies, since the cells which have been freed from the fatal infection are still living. Accordingly, if the amount of the virus (i.e., the number of individual viruses) is sufficient, it may advantageously be applied to the isolation of the mutated cells, said cells being mutated by their sensitivity to the virus, or the virus being mutated during their multiplication. In this manner, by using the agent (SP) of the invention, there can be provided a novel and useful means for studying viruses as follows:

(I) A virus that is negative to cellular degeneration can simply be detected and assayed from a mixture with host cells. This procedure is simple, being the same as the isolation of a virus that is positive to cellular degeneration from a mixture of said virus and host cells.

(II) It becomes possible to detect and isolate cells that have lost their sensitivity to the virus.

As described in detail hereinbefore, the fact that SP has a peculiar action against animal cells within the phase of DNA synthesis and against virus-infected cells or transformed cells provided the basis concerning the use of this substance as a carcinostatic agent. This assumption has been proven by in vivo experiments against EAC (Ehrlich ascites carcinoma), sarcoma 180 A and lymphocytic leukemia L 1210 of the mouse, respectively. Namely, a marked inhibition against the multiplication of the tumor cells of EAC by a dose of 1 to 2.5 mg/Kg of SP was observed. Moreover, a visible survival effect against sarcoma 180 A and lymphocytic leukemia L 1210 was further observed by a dose of 0.5 to 3 mg/Kg of SP.

The following constitutes a description as to the typical experimental facts from which the above findings have mainly been derived, as well as the acute toxicity studies of SP. Besides, since the effect and behavior of $SP_1$ and $SP_2$ are nearly equal, the data and facts concerning $SP_1$ are also applicable for $SP_2$ in the following description.

(1) Peculiar action of SP with respect to the animal cellular cycle.

(1-a) (Experimental materials)

Cells: $A_{31}$ cell (a clone derived from mouse BALB/C(strain))

Culture medium: Eagle NEM to which there was added 10% bovine fetal serum.

Agent: SP which was employed as a solution of phosphate buffer saline (PBS).

(1-b) (Experimental method)

In order to synchronize the cell cycle, the $A_{31}$ cells were preliminary incubated so as to cause contact inhibition. Then, a part of the cells was treated with trypsin and a fixed number of cells was spread on plastic plates. Thereafter, the agent was added thereto in the ratio of 4 μg or 6 μg to 1 ml of the medium every 4 hours and the numbers of living cells (differentiated with staining), DNA synthesis and the number of metaphase cells was measured, respectively, from time to time.

In addition, in this experiment, the measurement of the amount of DNA at every stage of the cell cycle was effected by means of a scintillation counter (Beckman Type LS 350). The said measurement of DNA was accomplished by adding 0.3 μci of [3H]-thymidine per plate, assaying the thymidine intake within 4 hours with a scintillation counter and comparing the amount of thymidine synthesized. The number of living cells was calculated after staining with 0.05 ml of 8% neutral red per plate by dispersing with trypsin, suspending into PBS and calculating the number of stained cells (regarding the stained as the living cells) by means of a Türk-Bürker calculation board.

(1-c) (Result)

Figure 1:
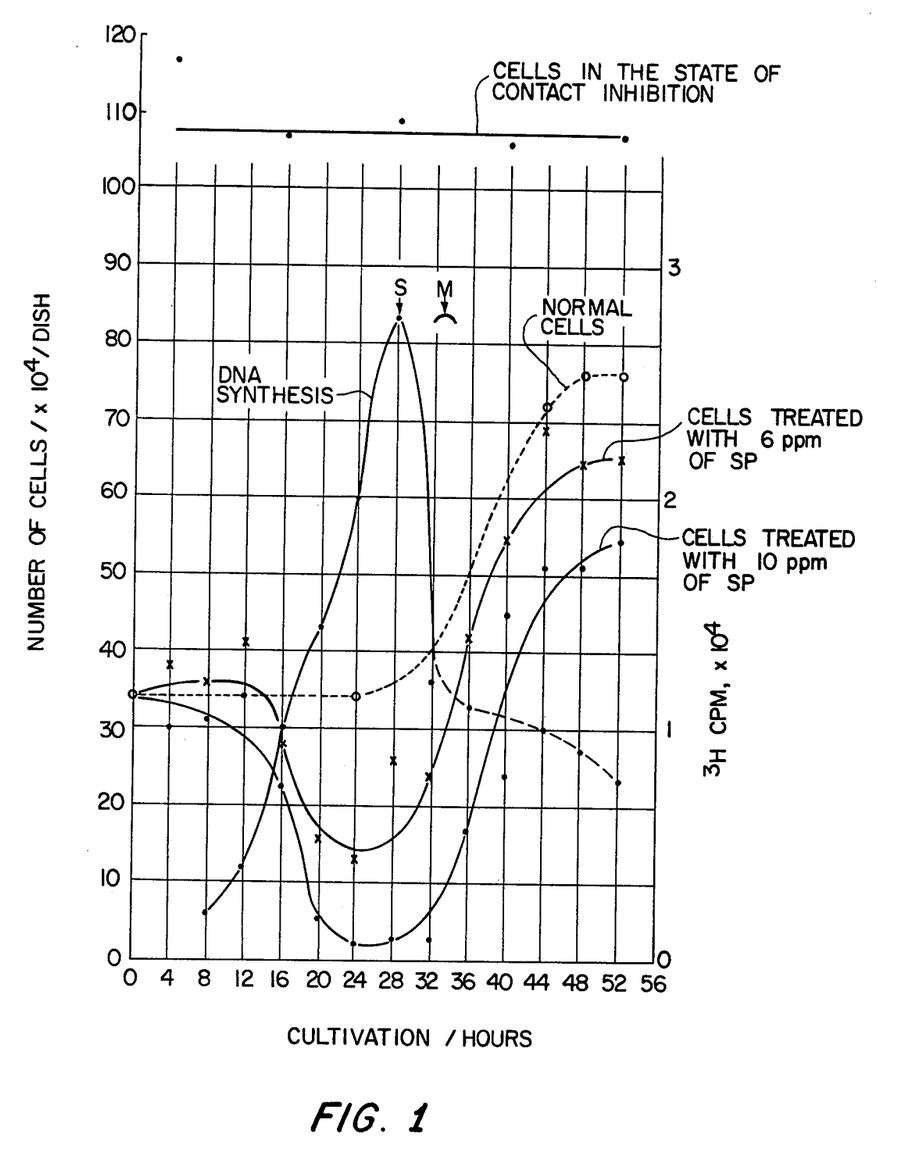
FIG. 1 shows plots of number of cells against cultivation time in hours for cells in the state of contact inhibition.

The result of this experiment is shown in the attached FIG. 1. As illustrated, the addition of 6 or 12 μg/ml of SP to the cells during the DNA-synthesis phase after 12 hours from the release of the contact inhibition causes death of the tested cells, but it does not affect the cells within the $G_1$ phase not having 12 hours elapsed from the release of the contact inhibition. And, the action of SP becomes weak with respect to the cells at the $G_2$- or M-phase, which have gone through the S-phase. On the contrary, it must be noted that the death of cells which are in the contact inhibition mode is not seen at all. From this result, it is obvious that SP will behave peculiarly against cells at the S-phase and will kill them.

Ordinarily, in the course of cellular multiplication, four phases such as are repeated, but the cells contact with each other as the result of this multiplication and thus can go into the state of contact inhibition. Thus, it may be presumed that SP will not influence normal cells but will selectively attack tumor cells during the S-phase. This fact further suggests that SP will be available as a peculiar inhibitor against the cell cycle and moreover as a biological agent, that is, as a synchronizer for the cultivation of cells.

(2) Action of SP against transformed cells (2-a) (Experimental materials)

Cells: $A_{31}$ (above mentioned), $LP_{14}$, $PV_4$ (transformant of $A_{31}$ by polyoma virus)

Culture medium: the same as (1-a) described above.

Agent: the same as (1-a) described above.

(2-b) (Experimental method)

$8.3 \times 10^4$ individual cells per plate are dispersed into the medium simultaneously with the addition of SP in the amount of 2 μg per ml of the culture. The incubation was continued for 3 days at 37° C. and then the culture medium was replaced with a new one. Thereafter, the same amount of SP was added into the medium and further incubated for four days. The final culture was dispersed with trypsin, and suspended into PBS, and the number of cells was calculated as described above under (1-a).

(2-c) (Result)

The result is shown in the following Table 3.

TABLE 3

| Cells | Amount of SP added (μg/ml medium) | | |
|---|---|---|---|
| | 0 | 2 | 4 |
| normal cell ($A_{31}$) | 285[1] | 290 | 220 |
| | (100.0)[2] | (101.8) | (77.2) |
| transformed cell ($LP_{14}$) | 310 | 238 | 63 |
| | (100.0) | (76.8) | (20.3) |

Notes:
[1] Number of cells per plate ($\times 10^4$/plate).
[2] The numbers enclosed by parentheses "( )" show the numerical percentages of the tested cells as compared to the control to which no SP was added.

(3) Fatal effect on the virus-infected cells (3-a) Experimental material

Cells: the same as (1-a) described above.

Virus: Murine leukemia virus (Mo-LuLV), a Molony strain of the mouse

Culture medium: Eagle MEM with 5% of fetal bovine serum

Agent: the same as (1-a) described above (3-b) (Experimental method)

$3 \times 10^5$ individual $A_{31}$ cells were dispersed into the medium, infected with MuLV simultaneously and incubated for 5 days at 37° C. After the contact inhibition which occurred was confirmed microscopically, 10 μg/ml of SP was added to the culture and the incubation was further continued for 4 hours. Then, the cells were stained with neutral red (the final concentration was 0.4%), and the number of living cells (using the stained cells as the parameter of living cells) was calculated with a Türk-Bürker calculation board as compared with the virus-infected $A_{31}$ cells.

(3-c) (Result)

The result is shown in the following Table 4.

TABLE 4

| cells | Number of living cells/dish[3] |
|---|---|
| normal cells ($A_{31}$ − MuLV) | $4 \times 10^5$ |
| Virus-infected cells ($A_{31}$ + MuLV) | $1.8 \times 10^3$ |

Note:
[3]The number of living cells after 4 days from the treatment with SP. From the above Table, it is clear that SP attacks the virus-infected cells and kills them. This phenomenon as to the increased sensitivity of the virus-infected virus to SP suggests the availability of SP for several scientific purposes, such as discrimination of the virus-infected cells and assay of the virus content or selection of virus mutants or the like.

(4) Carcinostatic action to animals (4-a): (Experimental materials)

Animal: mouse (Swiss albino)

Cell: Ehrlich ascites carcinoma cells (EAC)

(4-b): (Experimental method)

A number of Swiss albinos (male, mean body weight 21.6 g, age 5–6 weeks) was divided into 6 groups, each group being composed of 6 mice, and each mouse was inoculated intraperitoneally with 0.1 ml of the tumor cell suspension. The suspension contained $3.5 \times 10^7$ individual tumor cells per ml, which was prepared by diluting an ascites with PBS collected from a mouse cancerized by EAC after 7 days from the inoculation. From the next day of the inoculation, 1.0, 1.5, 2.0, 2.5 and 3.0 mg/Kg/0.2 ml, respectively, of SP was administered intraperitoneally for 7 days, day by day. The ascites developed after 8 days from the inoculation were collected, respectively, and the cell ratio (T/C%) was calculated.

(4-c): (Result)

The result of this experiment is summarized in Table 5.

TABLE 5

| SP administration dose (mg/kg) | T/C % (number of cells/mouse) | decision[4] |
|---|---|---|
| 0 | 100.0 (265 × 10⁶) | control |
| 1.0 | 42.9 (113 × 10⁶) | + |
| 1.5 | 30.3 (79.7 × 10⁶) | ++ |
| 2.0 | ( 22.3 (58.7 × 10⁶) | ++ |
| 2.5 | 12.6 (33.2 × 10⁶) | ++ |
| 3.0 | 9.1 (24.0 × 10⁶) | +++ |

Note:
[4]The decision is based on the following standard:
T/C %
100–66 : −
65–41 : +
40–11 : ++
10–0 : +++

As shown by the above Table 5, it is obvious that SP is highly active against the growth of the tumor cells with a dose of over 2.0 mg/Kg against EAC of the mouse.

(4′-a): (Experimental materials)

Animal: mouse (ICR strain, female, mean body weight 23.0 g, age 5 weeks)

Cell: sarcoma 180 A cell (4′-b): (Experimental method)

Six mice were organized into an organized group, and each mouse was inoculated intraperitoneally with 0.1 ml of the tumor cell suspension. The suspension contained $1 \times 10^8$ individual experimental tumor cells per ml. From the day of the inoculation, 0.5 mg per Kg body weight of SP was administered intraperitoneally five times a day.

(4′-c): (Result)

Figure 2A:
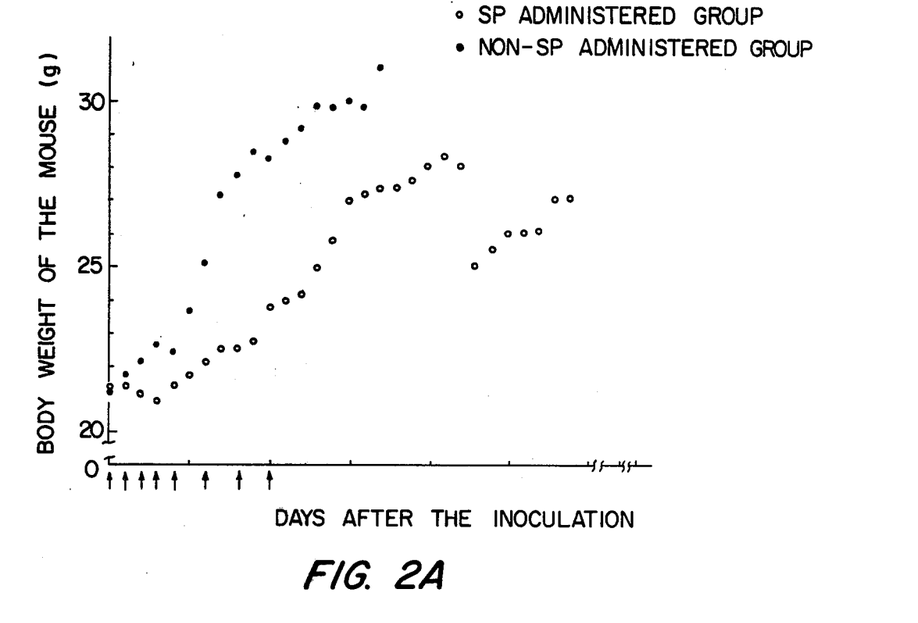
FIG. 2A shows body weights of mice plotted against the number of days after inoculation.
Figure 2B:
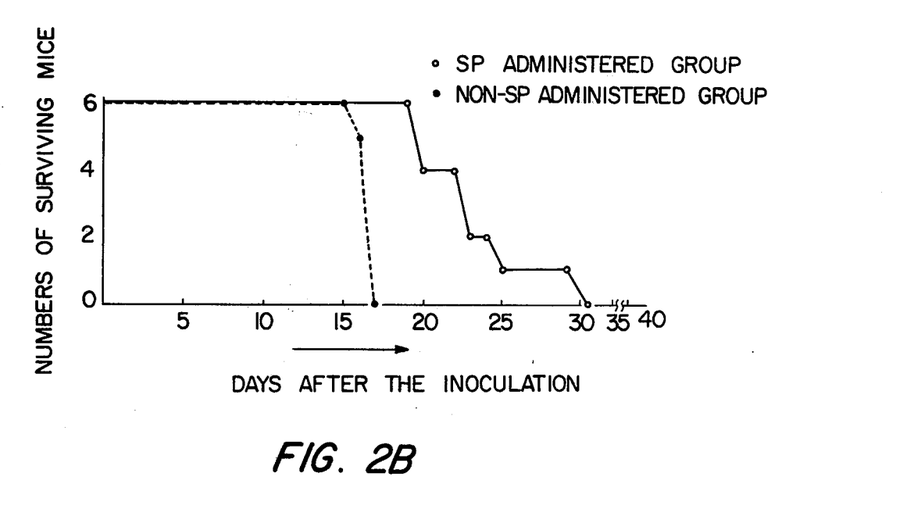
FIG. 2B shows the number of surviving mice plotted with respect to the number of days after inoculation.

The result is shown in the attached FIG. 2. As illustrated, the decrease of the body weights of the experimental mice is slight, or even decreases while the administration of SP is continued, but once said administration is stopped, there can be seen an abrupt increase of the body weights and, then, entire death of the group after 31 days from the date of the cancerization. Contrary to this, in the control group to which no SP was administered, there can be seen an abrupt increase in the body weights, and the animals entirely dies after 17 days from the cancerization. Therefore, it is clear that SP has a marked carcinostatic action against the tumor cells of sarcoma 180 A.

(5) Acute Toxicity to the Mouse (5-a) (Experimental material)

Animal: mice (CF #1, Swiss albino and BDF₁)

(5-b) (Experimental method)

CF#1 (male, mean body weight 26.2 g, age 5 weeks), Swiss albino (male, mean body weight 21.5 g, age 5–6 weeks) and BDF₁ (female, mean body weight 20.5 g, age 5–6 weeks) mice are divided into 4 groups. Each group is composed of 6 mice and destined amounts of SP, each dissolved into 0.2 ml of PBS, were injected into the intraperitoneum.

(5-c) (Result)

The result is shown in Table 6. The LD₅₀ of SP appears to be about 3.5 mg/Kg. This value looks small (i.e., the toxicity of SP is virulent), but is is almost the same as that of neocarzinostatin (having 109 constituent amino acids), which has already been put into clinical practice as a carcinostatic agent. Moreover, since the remaining toxicity of SP is so small, once the administration has stopped, the later condition of the surviving mice is quite similar to that of normal mice. Namely, no chronic toxicity has been observed.

Besides, judging from the above findings, the appropriate dose of SP need not be greater than 2.5 mg/Kg, desirably, 0.3-1.0 mg/Kg a day. Such a dose can be divided several times for a long-term administration.

TABLE 6

| CF #1[5] | | | Swiss albino[6] | | | BDF[7] | | |
|---|---|---|---|---|---|---|---|---|
| Actual amount (mg) | mg/Kg Body Weight | Number of Dead Mice | Actual amount (mg) | mg/Kg Body Weight | Number of Dead Mice | Actual amount (mg) | mg/Kg Body Weight | Number of Dead Mice |
| 0.065 | 2.48 | 0/6 | 0.044 | 2.05 | 0/6 | 0.040 | 1.95 | 0/6 |
| 0.85 | 3.24 | 2/6 | 0.066 | 3.07 | 3/6 | 0.060 | 2.93 | 1/6 |
| 0.105 | 4.01 | 4/6 | 0.088 | 4.09 | 5/6 | 0.080 | 3.90 | 3/6 |
| 0.125 | 4.77 | 6/6 | 0.110 | 5.12 | 6/6 | 0.100 | 4.88 | 6/6 |

Notes:
[5]$LD_{50}$: 3.63 mg/Kg
[6]$LD_{50}$: 3.15 mg/Kg
[7]$LD_{50}$: 3.74 mg/Kg (6) The action of SP against virus-infected and non-infected cells (6-a) (Experimental materials)
Cell: $A_{31}$ cell (a clone derived from mouse BALB/C)
Virus: Mo-MuLV (mouse leukemia virus of the Molony strain)
Culture medium: Eagle MEM with 5% fetal bovine serum.
Agent: the same as (1-a) described above (a mixture of $SP_1$ and $SP_2$)

(6-b) (Experimental method)
$3 \times 10^5$ individual $A_{31}$ cells per liter were dispersed, infected with the addition of a sufficient amount of MuLV and then incubated for 5 days at 37° C. After confirmation of the occurrence of contact inhibition microscopically, 10 μg/ml of SP was added to the medium. After 4 hours had elapsed, the cells were stained with neutral red (final concentration 0.4%), dispersed with trypsin and calculated on a Türk-Bürker calculation board regarding the stained cells as the living in comparison with non-infected $A_{31}$ cells.

(6-c) (Result)
The result is shown in Table 7.

TABLE 7

| | Number of living cells/plate* |
|---|---|
| Normal cell (−MuLV) | $4.0 \times 10^5$ (control) |
| Virus infected $A_{31}$-cell (+MuLV) | $1.8 \times 10^3$ |

Note:
*The number of living cells after 4 hours with the treatment by SP. As seen from the above table, it is apparent that SP very peculiarly attacks the virus-infected cells and kills them.

(7) Measurement of the amount of virus (7-a) (Experimental materials)
Cell: $A_{31}$ cell (the same as 1-a) XC cell (rat tumor cell cancerized by a plaque strain of Raus' sarcoma virus)
Virus: MuLV (the same as 1-a)
Culture medium: Eagle MEM (the same as 1-a)
Agent: the same as 1-a (7-b) (Experimental method)
The virus was diluted from $10^1$ to $10^9$ times stepwise, and then each diluted material was added onto respective plates having $5 \times 10^4$ individual $A_{31}$ cells. The incubation was carried out for 5 hours. After the occurrence of contact inhibition had been confirmed, the cells were disposed with trypsin and then divided equally into three parts, and further incubated at 37° C. to cause contact inhibition. The above procedures were repeated twice so as to cause an entire infection to all the cells.

To the plates of the cells being in the state of contact inhibition thus obtained, there was added 10 μg/ml (final concentration) of SP, and the cells were stained with neutral red after 24 hours in order to calculate the number of living cells as in Experiment 1.

On the other hand, a parallel experiment was conducted according to the XC-plaque method. To accomplish this experiment, the cells being in the state of contact inhibition were made stationary either by an irradiation with ultraviolet rays or by the addition of mitomycin C in the ratio of 5-10 μg/ml to the plate. There was then added $2-4 \times 10^6$ individual XC cells to each plate. After 20 hours, the cells were fixed with methanol and stained according to Gisma's method whereby the number of plaques formed were calculated.

(7-c) (Result)
The result is shown in Table 8.

TABLE 8

| Dilution degree of virus $(10^{-n})(n=)$ | 1 | 2 | 3 | 4 | 5 | 6 | 7 | 8 | 9 | None added (control) |
|---|---|---|---|---|---|---|---|---|---|---|
| The number of cells in SP-treated samples ($\times 10^4$/plate) (A) | 7.2 | 5.5 | 0.75 | 24.3 | 43.0 | 42.5 | 49.0 | 43.8 | 46.0 | 31.5 |
| The number of cells in non-SP-treated samples ($\times 10^4$/plate) (B) | 34.3 | 33.8 | 24.5 | 28.3 | 56.3 | 41.5 | 45.5 | 34.8 | 44.8 | 33.3 |
| A:B (A/B) | 0.21 | 0.16 | 0.03 | 0.86 | 0.76 | 1.27 | 1.08 | 1.26 | 1.03 | 0.95 |
| XC plaque method | +++ | +++ | ++ | + | − | − | − | − | − | − |

From the above table, it can be seen that in the regions wherein the dilution degree of the virus is lower than $10^{-4}$, a sudden decrease in the number of living cells is observed. This fact shows the presence of the virus-infected cells which are highly sensitive to SP. Namely, in this case, the amount of the virus before dilution may be presumed to be about $1 \times 10^{-4}$/ml and this presumption is in accordance with that by the XC-plaque method. Furthermore, according to this utilization of SP, the procedures are very simple, since it takes only 4 hours for the measurement and, moreover, the result is shown quantitatively. Therefore, this procedure is far more practical than the known XC-plaque method.

The present invention is based on the above findings and its gist exists in the use of SP as a carcinostatic agent and as an agent for the detection and determination of viruses. When this SP is used as a carcinostatic agent, it can be used as a unitary form of either pure or crude $SP_1$ or $SP_2$, or as a mixture thereof. The administration of SP may be realized by an injection such as an intravenous, intramuscular or subcutaneous injection, or by an oral administration form such as solutions, tablets, granules, troches or buccals and the like, or by a percutaneous administration form such as suppositories, or as an ointment for the skin. But, for injection use, it is naturally better to purify the SP as much as possible. For these pharmaceutical formulations, any pharmaceutically acceptable carriers, diluents, binders, thickeners, vehicles and the like which can conveniently be used for the compounding of pharmaceuticals may be used for the compounding of SP. Non-toxic vehicles such as liquid fats are appropriate for making SP suspensions for injection use.

SP may be converted to an acid addition salt with a physiologically acceptable acid such as hydrochloric, hydrobromic, sulfuric, maleic, fumaric, lactic, citric, malic, tartaric, succinic and glutaric acids or the like.

Generally speaking, the proper dose of SP is within a range of 0.5 to 2.0 mg per Kg of body weight per day, but it is apparent that such a dose is not conclusive and, therefore, the dosage amount should be varied in dependence upon the method and/or form of administration.

On the other hand, if said SP is used as an agent for the detection or determination of viruses, an appropriate concentration thereof is about 5–20 μg per ml of the culture medium. However, also in this case, the optimal concentration should, finally, be decided in dependence upon the kind of virus involved.

If the concentration is too low, it becomes impossible to entirely kill the virus-infected cells. If the concentration is too high, the remaining healthy cells (the non-infected cells) will fatally be affected.

Other than the above-mentioned, the polypeptide agent of the invention has the possibility of being utilized as an eliminator against so-called virus carriers, which are laterally existing, such as, for example, rabbit papiloma virus, influenza virus, yellow fever virus, measles virus, pig influenza virus from Paragonimus westermani and the like.

SP, the main component of the agent of the invention, forms a stable aqueous solution. Therefore, it is conveniently used in the form of an aqueous preparation with or without other components comprising a synthetic medium for the cultivation or incubation of the virus.

Figure 3:
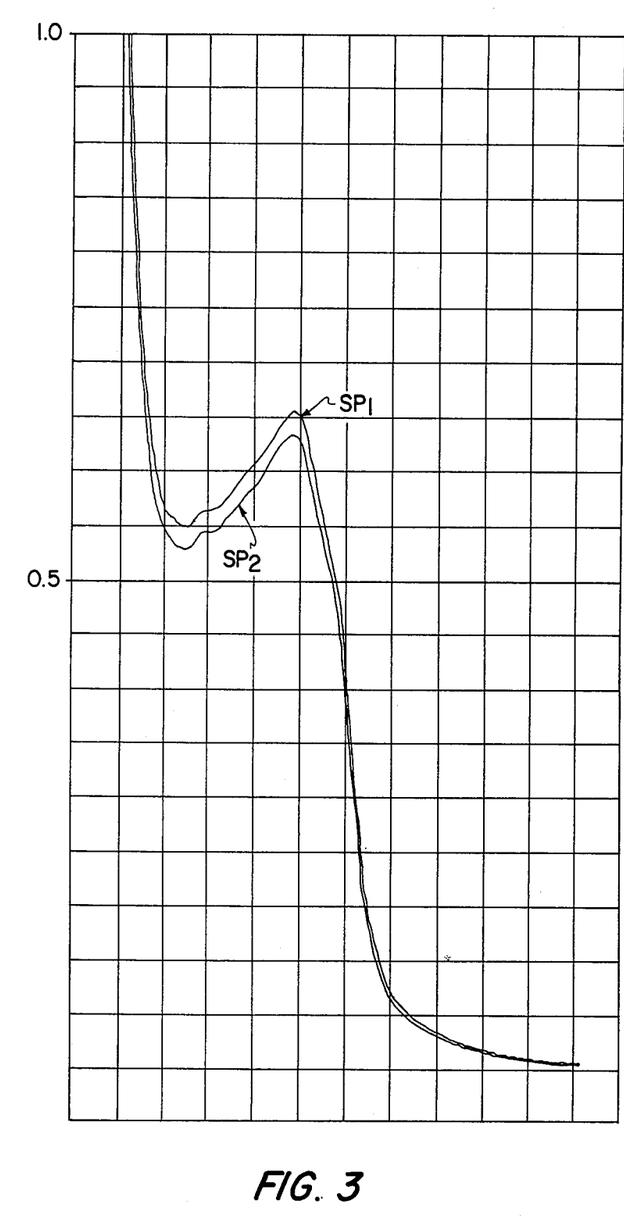
FIG. 3 shows the ultraviolet ray spectra of SP$_1$ and SP$_2$.
Figure 4:
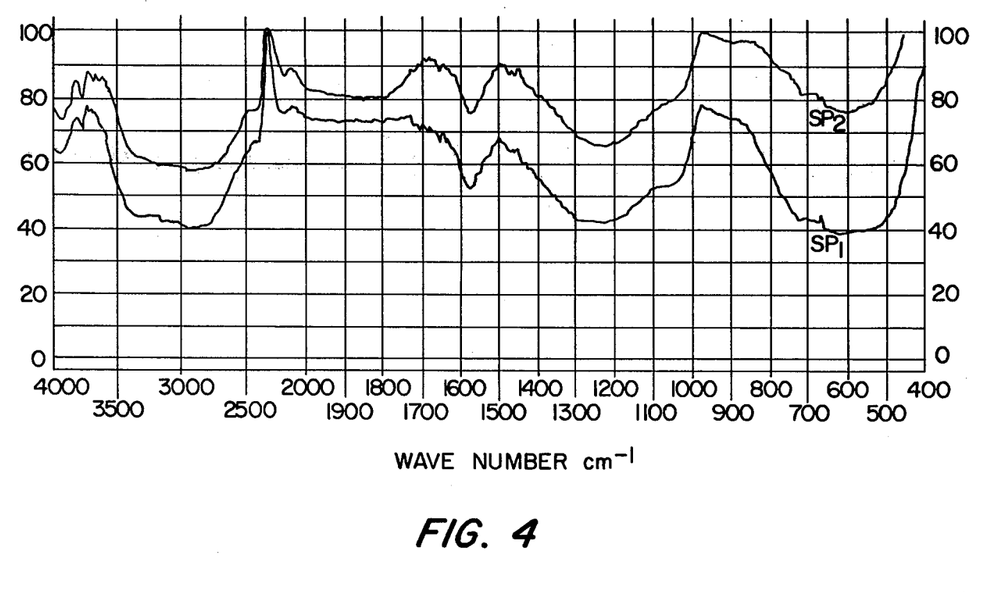
FIG. 4 illustrates the infrared spectra of SP$_1$ and SP$_2$.

FIGS. 1 and 2 as described hereinabove in connection with Experiments 1 and 4' show, respectively, (1) the behavior of SP against every stage of $A_{31}$ cells and (2) the survival effect and the effect against the increase of the body weight of the cancerized mice caused by the multiplication of the tumor cells with sarcoma 180 A (A being the rise and fall of mean body weight and B being the survival percentage). FIGS. 3 and 4 are described hereinabove.

The invention being thus described, it will be obvious that the same may be varied in many ways. Such variations are not to be regarded as a departure from the spirit and scope of the invention, and all such modifications are intended to be included within the scope of the following claims.

What we claim is:

1. A method for the quantitative detection of viruses comprising the steps of:
(a) contacting a virus infected cell culture with a polypeptide having the following formula:

wherein the symbols "Ala", "Arg", "Asn", "Cys", "Gln", "Gly", "Leu", "Lys", "Phe", "Pro", "Ser", "Thr", "Tyr" and "Val" indicate, respectively, the residues of the levo rotatory forms of alanine, arginine, asparagine, ½ cystine, glutamine, glycine, leucine, lysine, phenylalanine, proline, serine, threonine, tyrosine and valine, and wherein $R_1$–$R_5$ indicate (1) the residues of the L-amino acids lysine, asparagine, leucine, threonine and aspartic acid, respectively, or (2) wherein $R_1$ is arginine, $R_2$ and $R_5$ are glycine, $R_3$ is isoleucine and $R_4$ is serine, respectively, the symbols "=" represent —S—S— bonds and the arabic numerals included in the structural formula near certain amino acid residues constitute the sequence number of said amino acids in turn from the N-terminal and physiologically acceptable salts thereof, said polypeptide and salts thereof being present in an amount sufficient to selectively kill virus infected cells;
(b) incubating said virus infected cell culture for a period for time sufficient to selectively kill cells infected with said virus; and
(c) measuring the number of cells in said cell culture which are killed by said virus.

2. A method according to claim 1, wherein said polypeptide has the following formula:

wherein all of the symbols and numerals have the same meaning as described in claim 1.

3. A method according to claim 1, wherein said polypeptide has the following formula:

wherein all of the symbols and numerals have the same meaning as described in claim 1.

4. A method according to claim 1, wherein said virus infected cell culture is in a state of contact inhibition before it is treated with said polypeptide.

5. A quantitative method according to claim 4, wherein said measuring step includes staining said cells to selectively stain living or dead cells, respectively, in said culture.

6. A method according to claim 1, wherein said virus infected cells are treated with 5–20 Mg of said polypeptide per ml of cell culture medium.

7. A method according to claim 1, wherein said virus negatively affects the contact inhibition of said cells.

8. A method according to claim 1, wherein said virus is murine leukemia virus.

9. A method according to claim 1, wherein said cells are $A_{31}$ cells.

* * * * *